United States Patent [19]
Mayerhoefer et al.

[11] 4,021,464
[45] May 3, 1977

[54] BORIC ACID ESTERS

[75] Inventors: Horst Mayerhoefer, Oberwil; Wolfgang Müeller, Neuallschwil; Urs Sollberger, Follinsdorf, all of Switzerland

[73] Assignee: Sandoz Ltd., Basel, Switzerland

[22] Filed: Mar. 7, 1975

[21] Appl. No.: 556,303

Related U.S. Application Data

[62] Division of Ser. No. 276,395, July 31, 1972, Pat. No. 3,907,857.

[30] Foreign Application Priority Data

Aug. 5, 1971 Switzerland ............... 11525/71
Dec. 17, 1971 Switzerland ............... 18432/71

[52] U.S. Cl. .................. 260/462 R; 106/15 FP; 252/8.1; 260/45.7 R; 260/45.8 R; 260/45.9 AA; 260/DIG. 24
[51] Int. Cl.$^2$ ............................ C07F 5/04
[58] Field of Search ..... 260/462 R, 45.7 R, 45.8 R, 260/45.9 AA, DIG. 24; 252/8.1; 106/15 FP

[56] References Cited

UNITED STATES PATENTS

| | | | |
|---|---|---|---|
| 3,131,071 | 4/1964 | Hunter et al. | 106/15 |
| 3,189,565 | 6/1965 | Woods et al. | 260/462 R X |
| 3,250,797 | 5/1966 | Woods et al. | 260/462 R |
| 3,257,347 | 6/1966 | Woods et al. | 260/29.2 |
| 3,299,173 | 1/1967 | Roselli | 260/462 R X |
| 3,347,646 | 10/1967 | Gray et al. | 260/465 R X |
| 3,852,314 | 12/1974 | Hamanaka et al. | 260/45.8 R X |

FOREIGN PATENTS OR APPLICATIONS

| | | |
|---|---|---|
| 22,645 | 9/1968 | Japan |
| 402,259 | 7/1966 | Switzerland |

OTHER PUBLICATIONS

Lyons, The Chemistry and Uses of Fire Retardants, Wiley–Interscience, N.Y., pp. 86 to 89, 104, 105, (1970).

*Primary Examiner*—Helen M. S. Sneed
*Attorney, Agent, or Firm*—Gerald D. Sharkin; Richard E. Vila; Thomas C. Doyle

[57] ABSTRACT

The invention provides novel boric acid esters, useful as flame retardants.

15 Claims, No Drawings

BORIC ACID ESTERS

This is a division of application Ser. No. 276,395 filed July 31, 1972, now U.S. Pat. No. 3,907,857.

This invention relates to boric acid esters, useful as flame retardants.

More particularly, this invention provides compounds of formula I,

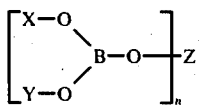

in which either X and Y are the same of different and each signifies a radical of formula II

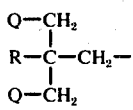

in which the radicals Q are the same or different and each signifies a chlorine or bromine atom, and R signifies an alkyl radical of 1 to 6 carbon atoms, or a radical $Q—CH_2—$, in which Q is as defined above, or X and Y together signify a radical of formula III,

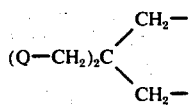

in which Q is as defined above, n signifies 1, 2, 3 or 4, and z signifies an n-valent hydrocarbon radical of up to 20 carbon atoms which consists of aromatic and/or saturated aliphatic units, which may be interrupted once or twice by an oxygen or sulphur atom, the imino radical or by an alkylimino radical of 1 to 6 carbon atoms, and which may be unsubstituted or substituted by one or more bromine or chlorine atoms, or hydroxyl or amino groups.

The invention also provides a process for the production of the compounds of formula I characterised by reacting, in either order, boric acid or a functional derivative thereof, with a compound of formula IV,

$(HO)_n Z$  IV in which Z and n are as defined above, and, where X and Y together signify a radical of formula III, with a compound of formula V,

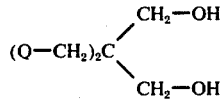

in which Q is as defined above, or, where X and Y each signify a radical of formula II, with a compound, or where X and Y are different, with appropriate compounds of formula VI,

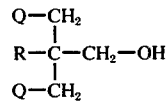

in which Q and R are as defined above.

Boric acid is especially suitable as starting material for the synthesis of compounds of formula I, as it is easily accessible and can be readily esterified. However, functional derivatives of boric acid, for instance boron trichloride or boric acid esters derived from lower alcohols, may also be used.

The process of the invention may be carried out in conventional manner. For example, if the starting material is boric acid, the process is suitably effected in an inert solvent and with heating of the starting materials, preferably at the reflux temperature of the reaction medium, the water formed in esterification then being carried off with the vapour of the boiling solvent. Suitable solvents are, for example, benzene, toluene, xylene and chlorobenzene. The rate of reaction can be increased by using a catalyst, in particular traces of strong acids of low volatility such as sulphuric or toluenesulphonic acid. If boric acid esters are employed in place of boric acid, the esterification reaction may be effected similarly, again suitably in the presence of traces of strong, non-volatile acids. If the selected functional derivative of boric acid is boron trichloride, it is again advisable to work with an inert solvent and in the presence of an acid-binding agent, for example pyridine or trialkylamines. The reactions may suitably be carried out at atmospheric pressure or at increased or reduced pressure. The reaction is conveniently started at a relatively low temperature and carried through to completion at higher temperatures. The reaction temperature may vary, for example from $-50°$ C to $200°$ C, preferably from $0°$ C to $150°$ C.

The resulting compounds of formula I may be isolated and purified using conventional techniques.

The compounds of formula IV, employed as starting materials are either known or may be produced in conventional manner from available materials. The compound of formula IV suitably may be a compound of formula V or VI. Other suitable compounds of formula IV include methanol, ethanol, isopropanol, butanol, benzyl alcohol, phenol, the cresols, phenols and cresols substituted by chlorine and, in particular, by bromine on the aromatic ring, alcohols substituted by chlorine and, in particular, by bromine, glycols, saturated aliphatic compounds containing 3 or 4 hydroxyl groups having a halogen atom bound to a carbon atom which in turn is bound to a tertiary carbon atom. Further examples of compounds of formula (IV) are ethylene glycol, 1,2-propylene glycol, 1,2-butylene glycol, 1,3-propylene glycol, 1,6-hexylene glycol, hydroquinone and, in particular, tetrabromohydroquinone, 2,2-bis-(4'-hydroxyphenyl)-propane, 2,2-bis-(3',5'-dibromo-4'-hydroxyphenyl)-propane, etanolamine, dimethylaminoethanol, ethyl mercaptoethanol, thiodiglycol, 1,1,1-tris-(hydroxymethyl)-ethane, 1,2,6-hexanetriol and pentaerythritol.

The compounds of formula V and VI employed as starting materials are either known or may be produced in conventional manner from available materials.

The compounds of formula I are useful as flame retardants for organic combustible materials, for example polyolefins, in particular polypropylene and polyethylene, polyesters, polymethyl methacrylates, polyphenylene oxides, polyurethanes, polyamides such as nylon, polystyrene, polypropylene oxide, ethyl cellulose, cellulose propionate, polyacrylonitrile, and copolymers such as acrylonitrilebutadiene-styrene copolymers. For this purpose, the compounds may be incorporated in the organic materials in conventional manner. The boric acid esters of formula (I) are especially suitable for incorporation in polypropylene and polyesters in the melt at high temperatures up to nearly 300° C, to be extruded in the form of filaments, films or as material for injection moulded articles.

In relation to known boric acid esters proposed for use as flame retardants, see for example Japanese Patent 22645/68, and U.S. Pat. No. 3,189,565, the compounds of the invention have the advantage of being relatively stable to heat. A further asset of the present compounds is their relatively small tendency to eliminate hydrogen halide after long storage periods or at high temperatures.

From the point of view of heat stability, particularly interesting compounds are those in which Z signifies a radical of formula II, and those derived from other alcohols whose hydroxyl groups are sterically hindered, for example from compounds of formula (IV) containing phenolic hydroxyl groups which are sterically hindered, for example by bromine or chlorine atoms in the two ortho-positions to the phenolic hydroxyl group.

Flame retardants often tend to migrate in the organic materials to which they are applied, which is highly undesirable. This migration can, in the compounds of the invention, be minimised by selecting suitable substituents. The effective life of flame retardants of relatively low molecular weight is in some cases somewhat low, as such compounds tend to sublime slowly out of the organic materials in which they have been incorporated. To increase the resistance to sublimation, a radical Z of high molecular weight can be selected or a value of $n$ greater than 1 can be chosen.

As regards flame-inhibiting action, particularly interesting compounds are those in which not only the radicals X and Y but also the radical Z contains chlorine or, preferably bromine atoms.

The preferred compounds of the invention are those substituted as follows:
a. X, Y and Z are the same or different and each signifies a radical of formula II and $n$ signifies 1.
b. X and Y signify jointly a radical of formula III, Z a straight, branched or cyclic alkyl or aralkyl radical of up to 12 carbon atoms, which may be interrupted by one or two oxygen or sulphur atoms, or by the imino radical or an alkyl-imino radical or 1 to 6 carbon atoms, and which is unsubstituted or substituted by a hydroxyl or amino group or by 1 to 5 bromine and/or chlorine atoms on a carbon atom bound to a tertiary carbon atom and/or on an aromatic ring, and $n$ stands for 1.
c. X and Y signify jointly a radical of formula III, Z an aryl radical of up to 12 carbon atoms which is unsubstituted or substituted by one or more alkyl radicals of 1 to 6 carbon atoms, or bromine and/or chlorine atoms, and $n$ signifies 1.
d. X and Y signify jointly a radical of formula III, Z a straight, branched or cyclic alkylene or aralkylene radical with 2 to 12 carbon atoms, which may be interrupted by one or two oxygen or sulphur atoms, or by the imino radical or an alkylimino radical of 1 to 6 carbon atoms, and which is unsubstituted or is substituted by a hydroxyl or amino group, or by 1 to 5 bromine and/or chlorine atoms on a carbon atom bound to a tertiary carbon atom and/or to an aromatic ring, and $n$ signifies 2.
e. X and Y signify jointly a radical of formula III, Z an arylene radical having at the most 12 carbon atoms, which may be interrupted by a lower alkylene radical and which is unsubstituted or substituted by one or more alkyl radicals of 1 to 6 carbon atoms, or bromine and/or chlorine atoms, and $n$ signifies 2.
f. X and Y signify jointly a radical of formula III, Z a trivalent radical of formula VII,

in which R is as defined above, and $n$ signifies 3.
g. X and Y signify jointly a radical of formula III, Z the tetravalent radical of formula VIII

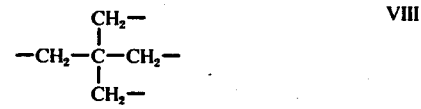

and $n$ signifies 4.

The amount of the compound of the invention which is employed for satisfactory flame retardation in a particular organic material may vary within wide limits, for example from 2 to 40, preferably about 3 to 10, weight per cent based on the organic material.

In the following Examples the parts and percentages are by weight and the temperatures in degrees centigrade.

EXAMPLE 1

3.7 Parts of boric acid and 58.5 parts of 2,2,2-(tris-bromomethyl)-ethanol are dissolved in 300 parts of toluene. The solution is boiled for 6 hours with reflux in a vessel with a water separator, during which time 3.2 parts of water are separated. On cooling to room temperature a white crystalline product settles out. Recrystallization from toluene yields 52 parts of the product with m.p. 136°–138°, which is equivalent to a yield of 83 %.

EXAMPLE 2

A solution of 52.4 parts of 2,2-(bis-bromomethyl)-1,3-propanediol and 12.35 parts of boric acid in 350 parts of benzene is boiled with reflux in a vessel with a water separator. In about 3 hours 8 parts of water are separated, on which 13.4 parts of monoethanolamine are slowly added. In the next 2 hours a further 1.5 parts of water are separated. On cooling to room temperature 54.2 parts of a white crystalline product, m.p. 161°–163°, settle out. This is equal to yield of approximately 82%.

EXAMPLE 3.

9 Parts of ethylene glycol are slowly added at −80° to 35 parts of boric trichloride, with subsequent stirring for 1 hour at room temperature under nitrogen. At this point 50 parts of toluene are added and then, with cooling, 73 parts of 2,2-(bis-bromomethyl)-1,3- propanediol in portions. The reaction mixture is stirred for 2 hours at room temperature and freed from solvent by the application of vacuum. 84 Parts of a colourless oil are obtained, which amounts to a yield of 96%.

EXAMPLE 4

A solution of 8.16 parts of boric acid and 51.9 parts of 2,2-(bis-bromomethyl)-1,3-propanediol in 240 parts of benzene is boiled for 5 hours with reflux in a vessel with a water separator. During this time 7.1 parts of water are separated. The solvent is removed by vacuum distillation and the oily residue freed from residual solvent in a high vacuum at 80° by the introduction of nitrogen. 52 parts of an almost colourless, highly viscous oil are obtained, which is equal to a yield of 98%.

EXAMPLE 5

In a nitrogen atmosphere 11.7 parts of boric trichloride are directed into 86 parts of dry toluene at −80°. In 30 minutes 26.2 parts of 2,2-(bis-bromomethyl)-1,3-propanediol are added, which goes into solution slowly with foaming. Stirring is continued for 30 minutes at −80°. The solution is allowed to cool slowly to room temperature, on which it loses its initial yellow colour to become almost colourless. After 15 hours the toluene is removed with vacuum leaving 31.8 grams of a yellow oil.

The formulae of the boric acid esters of formula (I) produced in the foregoing Examples and of other compounds produced in analogous manner is set out in Table 1 below.

$$\left[ \begin{array}{c} X-O \\ Y-O \end{array} B-O \right]_n Z \qquad (I)$$

| Ex. No. | X | Y | Z | n | m.p. |
|---|---|---|---|---|---|
| 1 | (BrCH$_2$)$_3$C—CH$_2$— | same as X | same as X | 1 | 136–138° |
| 2 | " | " | —CH$_2$CH$_2$NH$_2$ | 1 | 161–163° C |
| 3 | (BrCH$_2$)$_2$C(CH$_2$—)(CH$_2$—) | " | —CH$_2$CH$_2$OH | 1 | oil |
| 4,5 | " | " | (—CH$_2$)$_2$C(CH$_2$Br)$_2$ | 2 | Oil |
| 6 | " | " | —CH$_2$C(CH$_2$Br)$_3$ | 1 | 84–87° C |
| 7 | " | " | —CH$_2$CH$_2$N(CH$_3$)$_2$ | 1 | 80–84° C |
| 8 | " | " | —CH$_2$CH$_2$SC$_2$H$_5$ | 1 | Oil |
| 9 | " | " | (—CH$_2$)$_2$C(CH$_2$Cl)$_2$ | 2 | Oil |
| 10 | (ClCH$_2$)$_2$C(CH$_2$—)(CH$_2$—) | " | —C$_6$H$_4$— | 2 | Oil |
| 11 | (BrCH$_2$)$_2$C(CH$_2$—)(CH$_2$—) | " | —CH$_2$—C$_6$H$_4$—CH$_2$— | 2 | Oil |
| 12 | " | " | —C$_6$H$_4$—C(CH$_3$)$_2$—C$_6$H$_4$— | 2 | Oil |
| 13 | " | " | —C$_6$H$_4$— | 2 | 175–185° C |
| 14 | " | " | tetrabromo—C$_6$— | 2 | 200–210° C |
| 15 | " | " | —C$_6$H$_4$—C(CH$_3$)$_2$—C$_6$H$_4$— | 2 | Oil |
| 16 | " | " | dibromo-C$_6$H$_2$—C(CH$_3$)$_2$—C$_6$H$_2$-dibromo | 2 | Oil |
| 17 | As in Example 1. | | As in Example 14 | 2 | Oil |
| 18 | As in Example 1. | | As in Example 16 | 2 | Oil |

EXAMPLE 19

The compound of Example 1 or 4 is dissolved in trichloroethylene and applied from exhaust baths to a polypropylene fabric weighing 186 g per sq. metre. The fabric is freed from trichloroethylene in a vacuum drying oven at 80° for about 2 hours.

EXAMPLE 20

Polypropylene powder is intimately mixed with 8% of the boric acid ester of Example 4 or 9 by adding a 5% solution of the ester in carbon tetrachloride to the polypropylene powder in a rotating vacuum drum and running the drum to evaporate the solvent. The weight ratio is calculated so that after evaporation of the carbon tetrachloride, the polypropylene contains 8% of the boric acid ester. After regranulation, the melt is spun at 270° as continuous filament which is cold drawn and twisted to yarn. The yarn is converted into knitted fabric on a circular knitting machine.

What we claim is:

1. A compound of the formula

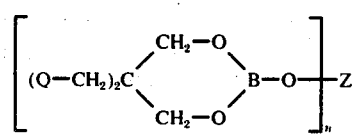

in which
each Q is, independently, chloro or bromo
n is 1, 2, 3 or 4, and
Z is selected from the group consisting of n-valent hydrocarbon groups of up to 20 carbon atoms which consist of aromatic and/or saturated aliphatic units, which may be interrupted once or twice by an oxygen or sulphur atom, the imino group or by an alkylimino group of 1 to 6 carbon atoms, and which may be unsubstituted or substituted by one or more bromine or chlorine atoms or hydroxyl or amino groups.

2. A compound of claim 1 in which Z is a straight, branched or cyclic alkyl or aralkyl group of up to 12 carbon atoms, which may be interrupted by one or two oxygen or sulphur atoms, or by the imino or an alkylimino group of 1 to 6 carbon atoms, and which is unsubstituted or substituted by an hydroxyl or amino group or by 1 to 5 bromine and/or chlorine atoms on a carbon atom bound to a tertiary carbon atom and/or on an aromatic ring, and n is 1.

3. A compound of claim 1, in which Z is an aryl group of up to 12 carbon atoms which is unsubstituted or substituted by one or more alkyl groups of 1 to 6 carbon atoms, or bromine and/or chlorine atoms, and n is 1.

4. A compound of claim 1, in which Z is a straight, branched or cyclic alkylene or aralkylene group with 2 to 12 carbon atoms, which may be interrupted by one or two oxygen or sulphur atoms, or by the imino group or an alkylimino group of 1 to 6 carbon atoms, and which is unsubstituted or is substituted by a hydroxyl or amino group, by 1 to 5 bromine and/or chlorine atoms on a carbon atom bound to a tertiary carbon atom and/or to an aromatic ring, and n is 2.

5. A compound of claim 1, in which Z is an arylene group having at the most 12 carbon atoms, which may be interrupted by a lower alkylene group and which is unsubstituted or substituted by one or more alkyl group of 1 to 6 carbon atoms, or bromine and/or chlorine atoms, and n is 2.

6. A compound of claim 1, in which Z is a trivalent group of formula VII

in which R is alkyl of 1 to 6 carbon atoms or a group Q—CH$_2$ and n is 3.

7. A compound of claim 1, in which Z is the tetravalent group of formula VIII,

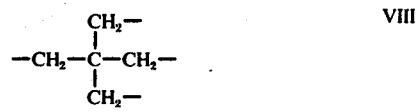

and n is 4.

8. A compound of claim 1 of formula

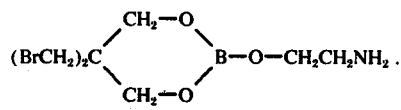

9. A compound of claim 1 of formula

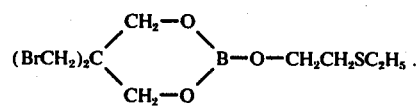

10. A compound of claim 1 of formula

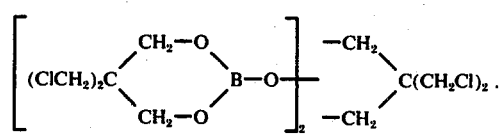

11. A compound of claim 1 of formula

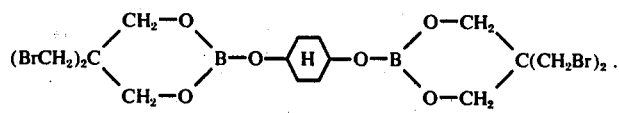

12. A compound of claim 1 of formula

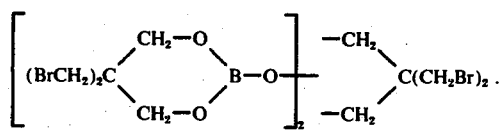

13. A compound of claim 1 of formula
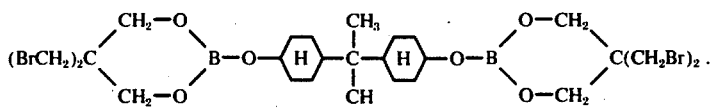
14. A compound of claim 1 of the formula
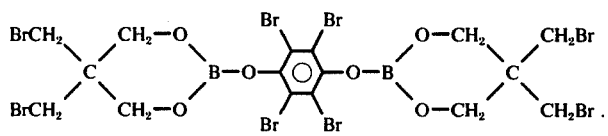
15. A compound of claim 1 of the formula
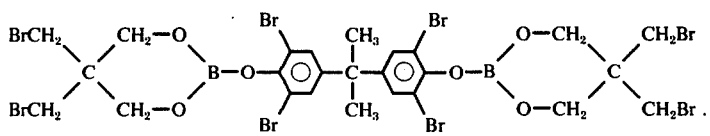
* * * * *